US011608530B1

(12) United States Patent
Lee et al.

(10) Patent No.: US 11,608,530 B1
(45) Date of Patent: Mar. 21, 2023

(54) SINGLE REACTION MULTIPLEX PCR PRIMER DESIGN FOR AMPLIFYING MULTIPLE HLA CLASS I AND II GENES

(71) Applicant: One Lambda, Inc., Canoga Park, CA (US)

(72) Inventors: Jar-How Lee, Los Angeles, CA (US); Katsuyuki Saito, Canoga Park, CA (US)

(73) Assignee: ONE LAMBDA, INC., Canoga Park, CA (US)

( * ) Notice: Subject to any disclaimer, the term of this patent is extended or adjusted under 35 U.S.C. 154(b) by 582 days.

(21) Appl. No.: 16/386,729

(22) Filed: Apr. 17, 2019

Related U.S. Application Data (60) Provisional application No. 62/659,240, filed on Apr. 18, 2018.

(51) Int. Cl.
*C12Q 1/6881* (2018.01)
*C12Q 1/686* (2018.01)
*C12Q 1/6806* (2018.01)

(52) U.S. Cl.
CPC ......... *C12Q 1/6881* (2013.01); *C12Q 1/686* (2013.01); *C12Q 1/6806* (2013.01); *C12Q 2600/16* (2013.01)

(58) Field of Classification Search
None
See application file for complete search history.

(56) References Cited

U.S. PATENT DOCUMENTS

| 2014/0206005 A1 | 7/2014 | Shiina et al. |
| 2016/0060695 A1 | 3/2016 | Shiina et al. |
| 2016/0208326 A1 | 7/2016 | Shiina et al. |
| 2017/0029885 A1 | 2/2017 | Shiina et al. |

FOREIGN PATENT DOCUMENTS

| WO | WO 2013/011734 A1 | 1/2013 |
| WO | WO 2014/181854 A1 | 11/2014 |
| WO | WO 2015/080226 A1 | 6/2015 |

OTHER PUBLICATIONS

Ozaki, Y. et al., Cost-efficient multiplex PCR for routine genotyping of up to nine classical HLA loci in a single analytical run of multiple samples by next generation sequencing, BMC Genomics, vol. 16:318, pp. 1-12 (Year: 2015).*
Hosomichi, K. et al., Phase-defined complete sequencing of the HLA genes by next-generation sequencing, BMC Genomics, vol. 14:355, pp. 1-16 (Year: 2013).*

(Continued)

*Primary Examiner* — Teresa E Strzelecka
(74) *Attorney, Agent, or Firm* — BakerHostetler (57) ABSTRACT

A method providing next generation sequencing (NGS)-based high-resolution HLA typing as a routine clinical test. The method uses a multiplex PCR primer design for amplifying multiple human leukocyte antigen (HLA) Class I and Class II genes in a single reaction for NGS. The test quality is improved and the protocol for typing multiple HLA genes is simplified because the number of amplification reactions are reduced nearly 10-fold, to yield a substantially equimolar ratio of individual HLA gene amplification products. The invention eliminates an amplicon pooling step, reducing the reagent cost, and required sample DNA quantity.

11 Claims, 2 Drawing Sheets

Specification includes a Sequence Listing.

(56) References Cited

OTHER PUBLICATIONS

Hosomichi, K. et al., Phase-defined complete sequencing of the HLA genes by next-generation sequencing, BMC Genomics, vol. 14:355, suppl. Fig. S1 (Year: 2013).*

Wang, C. et al., High-throughput, high-fidelity HLA genotyping with deep sequencing, PNAS, vol. 109, pp. 8676-8681 (Year: 2012).*

Buck, G.A. et al., Design Strategies and Performance of Custom DNA Sequencing Primers, Biotechniques, vol. 27, pp. 528-536 (Year: 1999).*

Henegariu, O. et al., Multiplex PCR: Critical Parameters and Step-by-Step Protocol, Biotechniques, vol. 23, pp. 504-511 (Year: 1997).*

Shiina, T. et al., Super high resolution for single molecule-sequence-based typing of classical HLA loci at the 8-digit level using next generation sequencers, Tissue Antigens, vol. 80, pp. 305-318 (Year: 2012).*

Morey, M. et al., A glimpse into past, present, and future DNA sequencing, Mol. Genet. Met., vol. 110, pp. 3-24 (Year: 2013).*

Kalendar, R et al., FastPCR Software for PCR, In Silico PCR, and Oligonucleotide Assembly and Analysis, Meth. Mol. Biol., vol. 1116, pp. 271-302 (Year: 2014).*

AllType™ and NXType™ NGS Reagents, Application Note, pp. 1-54 (Year: 2018).*

Vogiatzi; "Some considerations on the current debate about typing resolution in solid organ transplantation"; Transplantation Research; vol. 5(3); 2016; 6 pages.

Marsh et al.; "Nomenclature for Factors of the HLA System, 2000"; Human Immunology; vol. 62; 2001; p. 419-468.

"HLA Alleles Numbers"; http://www.hla.alleles.org/nomenclature/stats.html; Nomenclature;. Mar. 2019; accessed Jun. 14, 2019; 2 pages.

"Welcome to IPD-IMGT/HLA"; https://www.ebi.ac.uk/ipd/imqt/hla/; EMBL-EMBI; Apr. 2019; accessed Jun. 14, 2019; 2 pages.

"AllType™ and NXType™ NGS Reagents on Ion Chef™ & Ion S5™ XL System Application Note"; Revision 1; Jun. 28, 2017; 55 pages.

* cited by examiner

```
                        SEQUENCE LISTING

<160> NUMBER OF SEQ ID NOS: 32

<210> SEQ ID NO 1
   <211> LENGTH: 27
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 1
cttactctct ggcaccaaac tccatgg                                        27

<210> SEQ ID NO 2
   <211> LENGTH: 28
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 2
cctcctctct gcaaatgtca caatctgg                                       28

<210> SEQ ID NO 3
   <211> LENGTH: 29
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 3
ggttcccggt tgcaatagac agtaacaaa                                      29

<210> SEQ ID NO 4
   <211> LENGTH: 29
   <212> TYPE: DNA
   <213> ORGANISM: Artificial Sequence
   <220> FEATURE:
   <223> OTHER INFORMATION: Description of Artificial Sequence: Synthetic
         primer

<400> SEQUENCE: 4
ggttcgcggt tgcaatagac agtaacaaa                                      29

<210> SEQ ID NO 5
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctcccggtt gcaatagaca gtaacaaa                                            28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgggtccaa tttcacagac aaatgt                                              26

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgatgggtcc aatttcacag acaaatgt                                            28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gctcccggtt gcaatagacg gtaacaaa                                            28

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctcccggtt gcaacagaca gtaacaaa                                            28

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaacaattct agactatgga cccaattta caaacaaata                                40

<210> SEQ ID NO 11
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagagaacaa ggcctgaga                                                        19

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggtgctgggc ggatcctcct cca                                                   23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggtgcggggc ggatcctcct cca                                                   23

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cggtgctgga cggatcctcc tcca                                                  24

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcagcaaag ccctatttcc tcctctg                                               27

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggtcatctg catttcagct caggaatc                                              28

<210> SEQ ID NO 17
<211> LENGTH: 28
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 17
tggtcatctg catttcagct caggaatc          28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tgtggtcatc ttcacttcag ctcaggaatc          30

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atgtggtcat ctgcacttca gctcac          26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gacagggctt tccgcccttt cctg          24

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ggacagggct ttcctccctt tcctg          25

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcaggcatca cagaagagtg ataacca          27

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agcaggcgtt acagaaaagt gataacca                                        28

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aagatctctg ccatgaatga g                                               21

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gagctccgcc atgaatgag                                                  19

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctggagagg ctctgcgacc cgct                                            24

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
attctctctc tgcgtggtga gaaaacag                                        28

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cccagccatg ctgattcctc tccacc                                          26

<210> SEQ ID NO 29
<211> LENGTH: 32
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 29
ctcagaatag cgcctgacca tattaactac tc                                    32

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agttagttat cggtgttgtt gttgttatgc                                       30

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cagacatgca cacaccagag aagattcc                                         28

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgtcatcatc atgccacttc ccaattcc                                         28
```

SINGLE REACTION MULTIPLEX PCR PRIMER DESIGN FOR AMPLIFYING MULTIPLE HLA CLASS I AND II GENES

CROSS-REFERENCE TO RELATED APPLICATIONS

This application claims priority to U.S. Provisional Patent Application No. 62/659,240, filed Apr. 18, 2018, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Apr. 12, 2019, is named 110397_000003_SL.txt and is 7,525 bytes in size.

TECHNICAL FIELD

The present invention relates to methods and kits for simultaneously amplifying multiple or an entire compliment of human leukocyte antigen (HLA) Class I and Class II genes using a unique mixture of primer sequences.

BACKGROUND

In preparing a recipient for transplant of a donor organ, it is important to accurately predict potential donor-specific antibodies. Such donor-specific antibodies would cause the recipient to reject the organ based on hyperacute antibody production against the donor antibodies. To determine if such donor-specific antibodies are present, HLA typing is required for organ and stem cell transplant patients, and it is most advantageous to type multiple, preferably all, Class I and Class II HLA loci for all transplant-related tests. There are mandated requirements to type specific HLA-A, HLA-B, HLA-C, HLA-DRB1, HLA-DRB3, HLA-DRB4, HLA-DRB5, FLA-DQB1, HLA-DQA1 and DPB1 loci (United Network for Organ Sharing, 2014).

A goal for HLA testing is to minimize process steps and maximize efficiency by assigning each allele unequivocally at the molecular level in a single pass. This typing is typically accomplished using next generation sequencing (NGS) technology, also termed high-throughput sequencing, which revolutionized the molecular diagnosis of cancers, inherited diseases, and infectious diseases. NGS will likewise dramatically impact HLA typing in clinical settings.

Despite the fact that most HLA typing using DNA based methods examines only key exons corresponding to antigen-recognition-domain (ARD) of the HLA molecule, the recent development of NGS technology has proven the importance of using high-resolution typing as a routine test method. The importance of HLA typing for all class I and class II HLA loci using NGS technology has been reported recently as being critical for accurate prediction of potential donor specific antibodies in post-solid organ transplant patients to monitor and to avoid hyper acute antibody-mediated rejection caused by recipient antibodies against a graft (Vogiatzi Transplantation Research (2016) 5:3).

Given the advantages and clinical effectiveness of HLA typing with NGS technology, it is highly advantageous to provide a method to type multiple, preferably all, HLA loci for all transplant-related tests.

The ability of NGS technology to perform massively parallel sequencing that is clonal, i.e., individual reads of millions of single DNA segments, makes it possible to reconstruct allele sequences from overlapping gene fragments and identify the primary structure. This eliminates several limitations of current Sanger sequencing HLA typing technology, such as phase ambiguities arising from simultaneously sequencing two alleles, limitations in target coverage due to the need for target specific primers, individual sequencing reaction set-up for different regions. Another benefit of NGS is that the batch processing and high degree of base output allows higher throughput sequencing results at single allele resolution, eliminating the need for secondary typing to achieve higher resolution. These advantages allow reduced per sample cost and provide an unprecedented opportunity to remedy a long dilemma intrinsic to tissue typing: to assign each allele unequivocally at the molecular level in a single pass. Multiple HLA genes and multiple DNA samples can be sequenced on the same chip due to the large sequencing capacity of NGS platforms.

Achieving the goal of maximized efficiency and minimized process steps has, until the present invention, required multiple amplification reactions by a series of steps and a relatively large quantity of sample DNA to be typed to capture all HLA gene fragments containing essential sequence information. Each step requires additional reagents and introduces points at which errors may occur. The success of each amplification reaction in the polymerase chain reaction (PCR) had to be separately confirmed. Also required are subsequent clean up and quantification steps before all the amplicons from the same sample can be pooled for the next step in library preparation. This laborious process could potentially result in sample mix-up, contamination, quantification errors, and miscalculations in pooling that could jeopardize HLA typing results. Preparing multiple reactions per sample is costly in terms of both technologist time and reagents used for PCR and purification. Minimizing or eliminating the number of steps would reduce errors and save reagent and time costs.

SUMMARY

Disclosed herein are methods for genotyping at least one gene belonging to human leukocyte antigen (HLA) class I and at least one gene belonging to HLA class II using a mixture of both forward primers and reverse primers.

Also disclosed herein are methods for genotyping human leukocyte antigen (HLA), the method comprising (a) selecting at least one forward primer from SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, SEQ ID NO: 31, and selecting at least one reverse primer from SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, SEQ ID NO: 32 where the at least one forward primer and the at least one reverse primer flank at least one gene selected from genes belonging to HLA class I and/or HLA class II in a human genome sequence; (b) amplifying the at least one gene in a test sample in a single container to yield at least one amplified product; (c) determining the nucleotide sequence of the at least one amplified product; and (d) optionally carrying out a homology search within a database.

Further disclosed herein are systems for genotyping human leukocyte antigen (HLA) DNA from a test sample containing a nucleic acid molecule encoding HLA class I and/or HLA class II peptides, the system comprising (a) at least one forward primer from SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, SEQ ID NO: 31 and at least one reverse primer from SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, SEQ ID NO: 32 where the at least one forward primer and the at least one reverse primer flank at least one gene selected from genes belonging to HLA class I and/or HLA class II in a human genome sequence; and (b) a specific DNA polymerase.

Also disclosed here in are kits for genotyping human leukocyte antigen (HLA), the kit comprising (a) at least one forward primer from SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, SEQ ID NO: 31 and at least one reverse primer from SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, SEQ ID NO: 32, where the at least one forward primer and the at least one reverse primer flank at least one gene selected from genes belonging to HLA class I and/or HLA class II in a human genome sequence; (b) a specific DNA polymerase, and (c) instructions for determine HLA typing of a test sample using the kit.

Further disclosed herein are methods for DNA typing of human leukocyte antigens (HLA), comprising the steps of: (a) preparing sets of forward primers and reverse primers that hybridize specifically to an upstream region and a downstream region, respectively, of at least two genes, the genes selected from HLA Class I and HLA Class II in a genomic sequence of at least one of a transplant donor or a transplant recipient; (b) amplifying simultaneously by the polymerase chain reaction (PCR) under identical reaction conditions in a single container the at least two genes in a test sample of the at least one of a transplant donor or a transplant recipient using the forward primers and reverse primers; and (c) determining the nucleotide sequences of the amplified products. In some embodiments, the methods disclosed herein further comprise the step of performing a homology search of the nucleotide sequences within a database. In certain embodiments, the forward primer is selected from SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31 and the reverse primer is selected from SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

DETAILED DESCRIPTION OF ILLUSTRATIVE EMBODIMENTS

Provided herein are methods of simultaneously amplifying multiple or an entire compliment of human leukocyte antigen (HLA) Class I and Class II genes using a unique mixture of primer sequences. The described methods result in all genes being simultaneously amplified under identical conditions, in a single reaction and in a single container or tube. By providing for a process that amplifies all the required HLA gene fragments in one single reaction, the described methods eliminate error-prone steps as associated reagents used in those steps and improves methods for typing multiple human HLA genes. The methods thus beneficially types HLA loci for all transplant-related tests using next generation sequencing (NGS). This advantageously minimizes processing steps and maximizes efficiency by unequivocally assigning each allele at the molecular level in a single pass. The method is useful for both solid organ and stem cell transplants.

Class I human leukocyte antigen, abbreviated class I HLA, is an antigen or fragment of the antigen that comprises a $\beta 2$-microglobulin domain that is noncovalently bound to a heavy chain or fragment of the heavy chain. Class I HLAs are 57 kDa glycoproteins that are present on most nucleated human cells. Class I HLAs typically comprise a 45 kDa polypeptide heavy chain bound to a light chain that comprises a 12 kDa $\beta 2$-microglobulin domain. In embodiments, the heavy chain is noncovalently bound to the light chain. The heavy chain typically comprises three $\alpha$ subunits, a transmembrane domain, and a cytoplasmic tail. The $\alpha 1$ and $\alpha 2$ subunits form a binding groove for peptide ligand binding. The class I HLA heavy chain is encoded by one of three major genes: HLA-A, HLA-B and HLA-C, or one of three minor genes: HLA-E, HLA-F and HLA-G. Within each of these gene loci, there is allelic variation that contributes to the different forms, i.e., polymorphism, that class I HLA genes exhibit. A particular class I HLA can be categorized by the gene locus and by the particular allele from which the class I HLA is expressed.

Class II human leukocyte antigen, abbreviated class II HLA, is an antigen or fragment of the antigen that comprises a heterodimer of two glycosylated polypeptide chains that are noncovalently bound to each other. Class II HLA are polymorphic 61 kDa heterodimeric proteins that are present on the surface of specialized antigen presenting cells, e.g., B lymphocytes, dendritic cells, and macrophages. Class II HLA are divided into three subclasses: HLA-DP, HLA-DQ and HLA-DR. A native class II HLA typically comprises a $\alpha$ chain and $\beta$ chain bound to each other. In embodiments, the $\alpha$ chain and $\beta$ chain are noncovalently bound to each other. Each chain of a class II HLA comprises an extracellular domain, a transmembrane domain, and a cytoplasmic tail. The major class II HLA genes comprise: HLA-DPA1, HLA-PB1, HLA-DQA1, HLA-DQB1, HLA-DRA, DRB1, DRB3, DRB4 and HLA-DRB5, and each gene encodes either a $\alpha$ or $\beta$ chain. Similar to the class I HLA genes, each class II HLA gene comprise many alleles.

The HLA locus is highly polymorphic. As testament to this rapid progress, a December 2017 update by the WHO nomenclature Committee for Factors of the HLA System showed that there are 4,081 HLA-A alleles, 4,950 HLA-B alleles, 3,685 HLA-C alleles, 2,146 HLA-DRB1 alleles, 152

DRB3 alleles, 74 DRB4 alleles, 55 DRB5 alleles, 94 DQA1 alleles and 1,178 DQB1 alleles, with new alleles continuously being discovered (Nomenclature for Factors of the HLA System 2000, Hum. Immunol. 62(4):419-68, 2001, www.hla.alleles.org/nomenclature/stats.html).

"Same HLA allele" refers to two or more HLA molecules or fragments of HLA molecules that share similar structure and antigenic properties and that are derived from the same HLA gene loci and alleles.

As used herein, "different HLA allele" refers to HLA molecules or fragments of HLA molecules that possess different structure and antigenic properties and that are derived from different HLA gene loci and alleles.

As used herein, "single container" refers to a single reaction tube for performing PCR amplifications using any standard PCR cycling apparatus.

The disclosed methods significantly improve the quality of the test and simplifies the protocol for typing multiple HLA genes by reducing the number of amplification reactions by nearly 10-fold, to yield a substantially equimolar ratio of individual HLA gene amplification products. Beneficially, the invention eliminates an amplicon pooling step, reducing the cost of critical reagents such as DNA polymerase by 10-fold, and reducing required sample DNA quantity by nearly 10-fold compared to existing methods. These methods also facilitate adopting NGS-based high-resolution HLA typing to a routine clinical test by significantly reducing the labor, time, error-prone steps, and cost.

To date, there has been no established protocol to amplify Class I and Class II genes in a single reaction because of the nonhomologous nature between the Class I and Class II gene sequences.

The inventive primer mixture solves this problem and amplifies all loci of HLA Class I and Class II genes from a single DNA sample using a unique mixture of sequences as forward primers and reverse primers. Beneficially, only one PCR reaction per sample is required, and the requirements for amplicon pooling and normalization beads are eliminated. The inventive primer mixture and method of use thus facilitate the genotyping required for organ and stem cell transplants.

The inventive methods type multiple HLA genes, for example genes of up to eleven loci including classical HLA loci plus the alpha genes that are considered critical for organ/marrow transplant.

The initial steps of the NGS method for HLA typing using PCR-based target gene enrichment require the steps of gene-specific PCR, purification, quantification, and equimolar pooling of the amplification products per each sample. Each step is time and reagent consuming and is prone to errors. Thus reducing the number and/or complexity of the steps while achieving results is beneficial, because it facilitates results with less probability of error.

Figure 1:
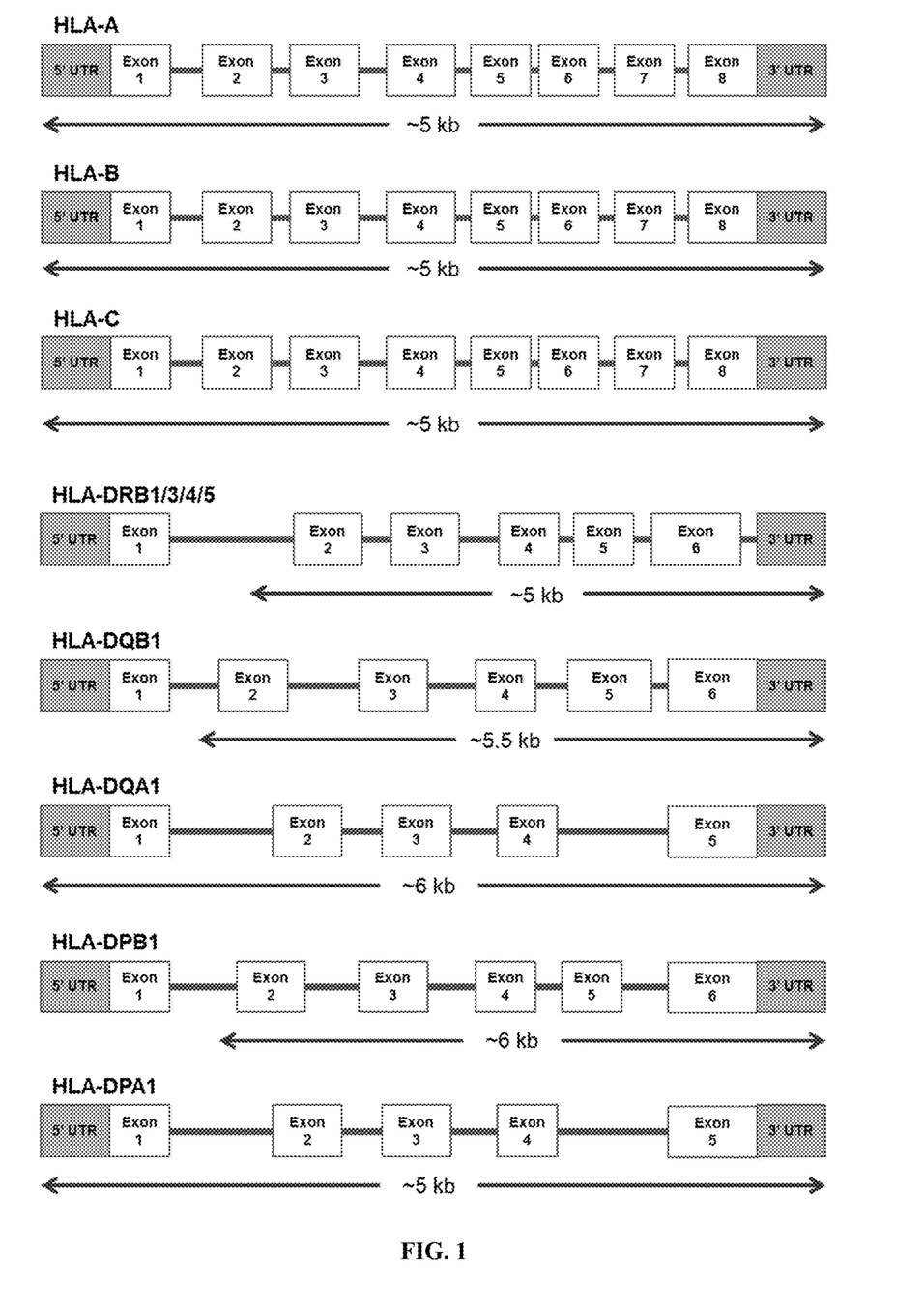
FIG. 1 illustrates a schematic of a single 11-loci multiplex reaction for Class I and Class II MCH genes combined.
Figure 2:
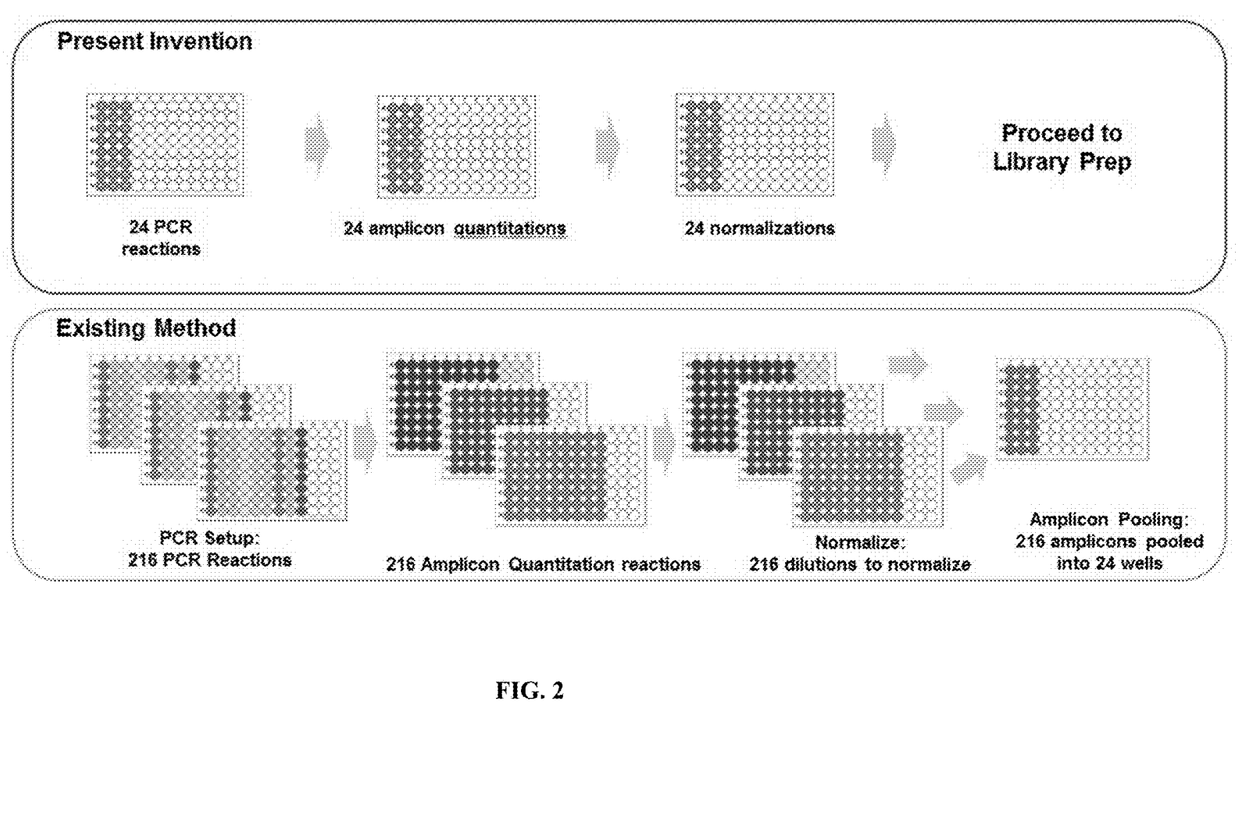
FIG. 2 illustrates a schematic of HLA typing using PCR-based target gene enrichment according to one embodiment of the invention.

To illustrate the benefits of the inventive method over current methods, for comparison, amplification of 11 HLA loci performed with single-plex primers would require preparing 11 PCR reactions per sample or, for a typical throughput of 24 sample assay, 264 PCR reactions per sample (assuming one PCR reaction per locus), as FIG. 2 shows. In addition, all of 264 reactions are subject to a magnetic bead-based purification step, followed by a quantification method, and an equi-molar pooling step, as FIG. 1 shows. The equi-molar pooling step involves transfer of different volumes per reaction to pool equimolar amounts of all PCR reactions into one volume per a sample. The total quantity of DNA must also meet the next step input standard (e.g., 100 ng of total DNA). Preparing multiple reactions per sample is not only costly in terms of reagents used for PCR and purification and employee time, it is prone to errors and cross-contamination risks that jeopardize the accuracy of HLA typing results.

FIG. 2 shows the benefits of the inventive method. The inventive method simplifies all of the above steps by combining all single-plex PCRs into one tube. Thus for a 24 sample assay, the number of tubes handled remains as 24, bypassing handling of 11 reaction tubes and bypassing dilutions and pooling of 264 tubes altogether. The formula for the primer mixture is adjusted so that the resulting PCR reaction yields a balanced amount of amplification product for each locus.

Prior to the described methods, there were no assays for multiplexed HLA Class I and Class II in a single tube reaction, notwithstanding prior attempts to design a multiplex assay for HLA Class I A, B, and C, or Class II DRB1, DRB3, DRB4, DRB5, DQB1, and DPB1 in single tube reactions. The inventive methods and systems thus significantly improve both processes and outcomes in HLA genotyping, particularly in the clinical setting where the demands for timeliness, efficiency, cost, and accuracy coexist.

Methods for genotyping human leukocyte antigen (HLA) select at least one forward primer at least one reverse primer that flank at least one gene belonging to HLA class I and/or HLA class II in a human genome sequence. The method then amplifies that gene in a test sample, e.g., blood or other tissue, in a single container to yield at least one amplified product. The nucleotide sequences of the amplified product is then determined. Optionally, one then performs a homology search of the sequences within a database of choice.

Disclosed herein are methods for genotyping at least one gene belonging to human leukocyte antigen (HLA) class I and at least one gene belonging to HLA class II using a mixture of both forward primers and reverse primers. Also disclosed herein are methods for genotyping all human leukocyte antigens using a mixture of both forward primers and reverse primers.

Selecting at least one forward primer and at least one reverse primer which flank a regions of a gene, including both exons and other regions such as introns, 5' and 3' untranslated regions, and a promoter region, may use primers which flank a class I antigen HLA-A, HLA-B, HLA-C, and/or primers which flank a class II antigens HLA-DRB1, HLA-DRB3, HLA-DRB4, HLA-DRB5, HLA-DQA1, HLA-DQB1, HLA-DPA1 and HLA-DPB1, and/or a set of primers which flank a region of exon 2 to a 3' untranslated region in HLA-DRB1, HLA-DRB3, HLA-DRB4, HLA-DRB5, HLA-DQB1, and HLA-DPB1. The forward primer may be selected from SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, SEQ ID NO: 31. The reverse primer may be SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, SEQ ID NO: 32.

At least one gene refers to at least one gene selected from the group consisting of HLA-A, HLA-B, HLA-C, HLA-DQA1, HLA-DQB1, HLA-DPA1, HLA-DRB1, HLA-DRB3, HLA-DRB4, HLA-DRB5 and HLA-DPB1. It includes combinations of two, three, four, five, six, seven, eight, nine or ten genes selected from the group consisting of HLA-A, HLA-B, HLA-C, HLA-DQA1, HLA-DQB1, HLA-DPA1, HLA-DRB1, HLA-DRB3, HLA-DRB4, HLA- DRB5 and HLA-DPB1, as well as a combination of all the eleven genes. In embodiments, the at least one forward primer at the at least one reverse primer amplify at least one gene encoding a class I antigen together with at least one gene encoding a class II antigen.

In embodiments, the method for genotyping HLA further comprises amplifying the at least one gene in a test sample in a single container to yield at least one amplified product. The amplification reaction may be achieved using polymerase chain reaction (PCR) amplification. The PCR amplification reaction may be performed in accord with a general protocol, e.g., (1) extracting DNA from a test sample, specifically depending on the form of the sample; (2) quantifying the extracted DNA and adding concentrations of primers sufficient and appropriate to prepare the reaction solution; (3) selecting reaction conditions, and performing PCR.

Using the inventive unique mixture of sequences as primers, a plurality of different genes is simultaneously amplified under the same conditions by a single reaction in a single tube.

In embodiments, the PCR reaction is a "touchdown" PCR reaction in which at least one additional primer is added to the PCR reaction to increase amplification specificity. The at least one additional primer may be selected from SEQ ID NO: 11, SEQ ID NO: 24 SEQ ID NO: 25.

In embodiments, the method for genotyping HLA includes determining the nucleotide sequence of the amplified product, e.g., using NGS. NGS technology permits performance of massively parallel sequencing that is clonal, i.e. individual reads of millions of single DNA segments, which makes it possible to reconstruct allele sequences from overlapping gene fragments and identify the primary structure.

In embodiments, the method for genotyping HLA further performs a homology search within a database, e.g., the IMGT-HLA database (www.ebi.ac.uk/ipd/imgt/hla/). A search for homology between the amplified product and the HLA alleles on the IMGT-HLA database may be performed, using the sequences of the candidate alleles as a reference. Mapping may be performed using GS Reference Mapper (Roche), and mapping states may be check visually to identify an HLA allele.

The test sample may be a biological sample including without limitation whole blood, blood derivatives, red blood cell concentrates, plasma, serum, fresh frozen plasma, whole blood derived platelet concentrates, apheresis platelets, pooled platelets, intravenous gamma-globulin, cryoprecipitate, cerebrospinal fluid, tissues, cells such as epithelial cells, such as those collected from the buccal cavity, stem cells, leukocytes, neutrophils, eosinophils, basophils, macrophages, etc. The biological sample may be from a human donor of tissue or cells intended for transplantation or a human donor of blood or blood derivatives intended for transfusion. The biological sample may from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

The specific DNA polymerase used in the inventive method is not limited and may be commercially available, e.g., PrimeSTAR GXL DNA Polumerase, Tks Gflex DNA Polymerase, TaKaRa LA Taq (TaKaRA BIO INC.); Long PCR Enzyme Mix (Thermo Fisher Scientific Inc.), including protocols that permit erythrocyte use such as Phusion Blood Direct PCR (Thermo Fisher Scientific Inc.) and MyTaq Blood-PCR Kit (Bioline.com).

Kits for performing the inventive method may contain additional components for genotyping HLA in a test sample including nucleotides, reaction buffers, PCR tubes, etc. The kit may be labeled with a listing of contents and/or instructions for use, and/or the kit may contain a package insert with instructions for use.

Other aspects and advantages of the invention will be understood from the following illustrative example.

EXAMPLE

Single Eleven-Loci Multiplex Reaction

As shown in FIG. 1, the inventive methods use a primer mixture that amplifies multiple loci of HLA Class I and II genes from a single DNA sample to facilitate the genotyping required for organ and stem cell transplants. Genes of up to eleven loci, including classical HLA loci plus the alpha genes that are considered critical for organ/marrow transplant, are typed simultaneously. Despite the fact that most HLA typing using DNA based methods examines only key exons corresponding to antigen-recognition-domain (ARD) of the HLA molecule, the development of NGS technology has highlighted the importance of using high-resolution typing as a routine test method.

The ability of NGS technology to perform massively parallel sequencing that is clonal makes it possible to reconstruct allele sequences from overlapping gene fragments and identify the primary structure. This eliminates several limitations of current Sanger sequencing HLA typing technology, such as phase ambiguities arising from simultaneously sequencing two alleles, limitations in target coverage due to the need for target specific primers, individual sequencing reaction set-up for different regions. The batch processing and high degree of base output in NGS technology allows higher throughput sequencing results at single allele resolution, eliminating the need for secondary typing to achieve higher resolution.

The initial steps of the NGS method for HLA typing using polymerase chain reaction (PCR)-based target gene enrichment require gene-specific PCR followed by purification, quantification, and equimolar pooling of the amplification products per each sample. For comparison, amplification of 11 HLA loci performed with single-plex primers, would require setting up 11 PCR reactions per sample or for a typical throughput of 24 sample assay, 264 PCR reactions must be prepared (FIG. 2). In addition, all 264 reactions are subject to a magnetic bead based purification step followed by a quantification method and an equimolar pooling step (FIG. 1). The equimolar pooling step involves transfer of different volumes per reaction to pool equimolar amounts of all PCR reactions into one volume per a sample. The total quantity of DNA must also meet the next step input standard (e.g., 100 ng of total DNA).

As shown in FIG. 2, the inventive method simplifies all of the above steps by combining all single-plex PCRs into one tube. Thus for a 24 sample assay, the number of tubes one handled remains as 24 bypassing handling of 11 reaction tubes and dilutions and pooling of 264 tubes altogether.

Amplification Procedure:
Required materials and equipment
  AllType™ 11-Loci primer mix (One Lambda)
  AllType™ buffer, dNTPs, and polymerase (One Lambda)
  96-Well 0.2 mL PCR plate and plate seals
  1.5-mL Eppendorf LoBind™ tubes
  PCR plate cooler and ice
  Nuclease-free water (1) Before starting, turn on a thermal cycler to allow the heated lid to reach temperature.
(2) Thaw DNA, AllType primer mix, dNTP and buffer at room temperature. If precipitate is present in the AllType buffer warm it at 37° C. and vortex until clear. Place the polymerase on ice when not in use.
(3) Once thawed, briefly vortex the dNTP, buffer, and primer mix.
(4) Prepare a 96-well 0.2 mL PCR plate so that it will accommodate the number of samples that are to be amplified.
(5) Using 1.5-mL Eppendorf LoBind tubes, create an amplification master mix. To determine the total volume of each reagent, multiply the volume of each reagent listed below by the number of samples to be tested and add an additional 15% as overage. Add the reagents to the 1.5-mL Eppendorf LoBind tubes in the order as provided in Table 1.
  Note: Amplification reaction volume should not be altered from the volumes directed in steps 6 & 8. AllType reagents are optimized for use in a 20 µL reaction volume. Sub-optimal results will occur if the volumes are altered.

TABLE 1

| Order | Component | AllType 11-Loci Volume (per reaction) |
|---|---|---|
| 1 | Nuclease-free water | 6.6 µl |
| 2 | AllType buffer | 4 µl |
| 3 | AllType dNTPs | 1.6 µl |
| 4 | AllType primer mixes | 5 µl |
|  | Total | 17.2 µl |

(6) Vortex the amplification master mix for 10 seconds, pulse-spin, and place on ice until ready to proceed.
(7) When ready to proceed add the polymerase to the amplification master mix at a volume of 0.8 µl per reaction. Mix well by pipetting up and down 15-20 times. Do not vortex the finished amplification master mix. Include a 15% overage when calculating the volume of polymerase to use.
(8) Retrieve the 96-well 0.2 mL PCR plate containing DNA and aliquot 18 µL of the amplification master mix to each reaction, taking special care so as not to cross-contaminate reactions.
(9) Seal the plate with a tray seal, pulse-vortex, and pulse spin the plate.
(10) Load the 96-well 0.2 mL PCR plate into a thermal cycler and cover the plate with a PCR pressure pad appropriate for your machine. Run the following program (to amplify the genomic DNA targets) as provided in Table 2. Set reaction volume to 20 µL. For GeneAmp® PCR System 9700, set "ramp speed" to the 9600 program. For other systems, consult the manufacturer's documentation to adjust ramp speed to simulate the GeneAmp 9600 program. Use of a significantly different ramp speed will affect amplification efficiency.

TABLE 2

Amplification PCR Program

| Step | Temperature | Time | # of Cycles |
|---|---|---|---|
| Step 1: | 94° C. | 2 minutes | 1 |
| Step 2: | 98° C. | 10 seconds | 22 |
|  | 69° C. | 3 minutes |  |
| Step 3: | 98° C. | 10 seconds | 8 |
|  | 60° C. | 3 minutes |  |
| Step 4: | 4° C. | ∞ | 1 |

The formula for the primer mixture is adjusted so that the resulting PCR reaction yields a balanced, substantially equimolar, amount of amplification product for each locus. The primer sequences provided in Table 3 were selected based on sequence comparison between known target HLA gene sequences and known pseudogene sequences to minimize off-target gene amplification. The primer sequences were further refined for theoretical melting temperature, and GC content. Finally, the sequences were experimentally tested for functionality in presence of another 11 loci primer mix. Overall performance of the primer for equimolar amplification product, sequence coverage numbers amongst 11 loci (locus balance), and allele specific coverage (allele balance) were reviewed and adjustments were made to optimize the parameters based on experimentally obtained sequencing data. Although there have been prior attempts to design a multiplex assay for HLA Class I A, B, and C or Class II DRB1, DRB3, DRB4, DRB5, DQB1, and DPB1 in single tube reactions, none have achieved multiplexing HLA Class I and Class II in a single tube reaction.

TABLE 3

| HLA Class I or Class II gene | Primer Name | Primer Length | Primer Sequence (5'-3') | SEQ ID NO: |
|---|---|---|---|---|
| HLA-A | HLA-A 1 | 27 | CTTACTCTCTGGCACCAAACTCCATGG | 1 |
| HLA-A | HLA-A 2 | 28 | CCTCCTCTCTGCAAATGTCACAATCTGG | 2 |
| HLA-B | HLA-B 1 | 29 | GGTTCCCGGTTGCAATAGACAGTAACAAA | 3 |
| HLA-B | HLA-B 2 | 29 | GGTTCGCGGTTGCAATAGACAGTAACAAA | 4 |
| HLA-B | HLA-B 3 | 28 | GCTCCCGGTTGCAATAGACAGTAACAAA | 5 |
| HLA-B | HLA-B 4 | 26 | ACGGGTCCAATTTCACAGACAAATGT | 6 |

TABLE 3-continued

| HLA Class I or Class II gene | Primer Name | Primer Length | Primer Sequence (5'-3') | SEQ ID NO: |
|---|---|---|---|---|
| HLA-B | HLA-B 5 | 28 | TGATGGGTCCAATTTCACAGACAAATGT | 7 |
| HLA-C | HLA-C 1 | 28 | GCTCCCGGTTGCAATAGACGGTAAACAA | 8 |
| HLA-C | HLA-C 2 | 28 | GCTCCCGGTTGCAACAGACAGTAACAAA | 9 |
| HLA-C | HLA-C 3 | 40 | GAACAATTCTAGACTATGGACCCAATTTTACAAACAAATA | 10 |
| HLA-A, B, C | HLA-A, B, C | 19 | CAGAGAACAAGGCCTGAGA | 11 |
| HLA-DRB1,3,4,5 | HLA-DRB 1 | 23 | GGTGCTGGGCGGATCCTCCTCCA | 12 |
| HLA-DRB1,3,4,5 | HLA-DRB 2 | 23 | GGTGCGGGGCGGATCCTCCTCCA | 13 |
| HLA-DRB1,3,4,5 | HLA-DRB 3 | 24 | CGGTGCTGGACGGATCCTCCTCCA | 14 |
| HLA-DRB1,3,4,5 | HLA-DRB 4 | 27 | CTCAGCAAAGCCCTATTTCCTCCTCTG | 15 |
| HLA-DRB1,3,4,5 | HLA-DRB 5 | 28 | TGGTCATCTGCATTTCAGCTCAGGAATC | 16 |
| HLA-DRB1,3,4,5 | HLA-DRB 6 | 28 | TGGTCATCTGCATTTCAGCTCAGGAATC | 17 |
| HLA-DRB4 | HLA-DRB 7 | 30 | TGTGGTCATCTTCACTTCAGCTCAGGAATC | 18 |
| HLA-DRB5 | HLA-DRB 8 | 26 | ATGTGGTCATCTGCACTTCAGCTCAC | 19 |
| HLA-DQB1 | HLA-DQB 1 | 24 | GACAGGGCTTTCCGCCCTTTCCTG | 20 |
| HLA-DQB1 | HLA-DQB 2 | 25 | GGACAGGGCTTTCCTCCCTTTCCTG | 21 |
| HLA-DQB1 | HLA-DQB 3 | 27 | GCAGGCATCACAGAAGAGTGATAACCA | 22 |
| HLA-DQB1 | HLA-DQB 4 | 28 | AGCAGGCGTTACAGAAAAGTGATAACCA | 23 |
| HLA DQB1 | HLA-DQB 5 | 21 | AAGATCTCTGCCATGAATGAG | 24 |
| HLA DQB1 | HLA-DQB 6 | 19 | GAGCTCCGCCATGAATGAG | 25 |
| HLA-DPB1 | HLA-DPB 1 | 24 | CCTGGAGAGGCTCTGCGACCCGCT | 26 |
| HLA-DPB1 | HLA-DPB 2 | 28 | ATTCTCTCTCTGCGTGGTGAGAAAACAG | 27 |
| HLA-DPA1 | HLA-DPA 1 | 26 | CCCAGCCATGCTGATTCCTCTCCACC | 28 |
| HLA-DPA1 | HLA-DPA 2 | 32 | CTCAGAATAGCGCCTGACCATATTAACTACTC | 29 |
| HLA-DPA1 | HLA-DPA 3 | 30 | AGTTAGTTATCGGTGTTGTTGTTGTTATGC | 30 |

TABLE 3-continued

| HLA Class I or Class II gene | Primer Name | Primer Length | Primer Sequence (5'-3') | SEQ ID NO: |
|---|---|---|---|---|
| HLA-DQAI | HLA-DQA 1 | 28 | CAGACATGCACACACCAGAGAAGATTCC | 31 |
| HLA-DQAI | HLA-DQA 2 | 28 | TGTCATCATCATGCCACTTCCCAATTCC | 32 |

The embodiments shown and described in the specification are only specific embodiments of inventors who are skilled in the art and are not limiting in any way to the location in the body, nanoparticle type or composition, disease process, source of energy, medication, gene, etc. Therefore, various changes, modifications, or alterations to those embodiments may be made without departing from the spirit of the invention in the scope of the following claims. The references cited are expressly incorporated by reference herein in their entirety.

What is claimed:

1. A method for genotyping human leukocyte antigen (HLA), the method comprising
    (a) amplifying HLA class I and HLA class II genes in a test sample in a single container to yield at least two amplified products using forward primers and reverse primers,
        wherein the forward primers and the reverse primers specifically hybridize regions which flank at least one gene selected from genes encoding HLA class I antigens HLA-A, HLA-B, HLA-C, and at least one gene selected from genes encoding HLA class II antigens HLA-DQA1 and HLA-DPA1, and a region of exon 2 to a 3' untranslated region in at least one of HLA-DRB11, HLA-DRB3, HLA-DRB4, HLA-DRB5, HLA-DQB1, and HLA-DPB1, and
        wherein amplifying comprises amplifying by polymerase chain reaction (PCR) comprising a first set of at least 22 amplification cycles, each amplification cycle within the first set comprising a temperature of 98° C. for 10 seconds and 69° C. for 3 minutes, followed by a second set of at least eight amplification cycles, each amplification cycle of the second set comprising a temperature of 98° C. for 10 seconds and 60° C. for 3 minutes;
    (b) determining the nucleotide sequence of the at least one amplified product; and
    (c) optionally carrying out a homology search within a database.

2. The method of claim 1 wherein the forward primers for the HLA class I genes consist of SEQ ID NO: 1, SEQ ID NO: 3, SEQ ID NO: 4, SEQ ID NO: 5, SEQ ID NO: 8, and SEQ ID NO: 9, and wherein the reverse primers for the HLA class I genes consist of SEQ ID NO: 2, SEQ ID NO: 6, SEQ ID NO: 7, SEQ ID NO: 10, and SEQ ID NO: 11; and wherein the forward primers for the HLA class II genes consist of SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31, and wherein the reverse primers for the HLA class II genes consist of SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

3. The method of claim 1 wherein the forward primers comprise at least two primers selected from SEQ ID NO: 1, SEQ ID NO: 3, SEQ ID NO: 4, SEQ ID NO: 5, SEQ ID NO: 8, SEQ ID NO: 9, SEQ ID NO: 28, and SEQ ID NO: 31.

4. The method of claim 1 wherein the reverse primers comprise at least two primers selected from SEQ ID NO: 2, SEQ ID NO: 6, SEQ ID NO: 7, SEQ ID NO: 10, SEQ ID NO: 11, SEQ ID NO 29, SEQ ID NO: 30, and SEQ ID NO: 32.

5. The method of claim 3 wherein the forward primers for the HLA class I antigens are selected from SEQ ID NO: 1, SEQ ID NO: 3, SEQ ID NO: 4, SEQ ID NO: 5, SEQ ID NO: 8, and SEQ ID NO: 9, and wherein the reverse primers for the HLA class I antigens are selected from SEQ ID NO: 2, SEQ ID NO: 6, SEQ ID NO: 7, SEQ ID NO: 10, and SEQ ID NO: 11; and wherein the forward primers for the HLA class II antigens are selected from SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31, and wherein the reverse primers for the HLA class II antigens are selected from SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

6. A method for DNA typing of human leukocyte antigens (HLA), comprising the steps of
(a) amplifying with a set of forward primers and reverse primers that specifically hybridize regions which flank at least one gene selected from genes encoding HLA class I antigens HLA-A, HLA-B, HLA-C, and at least one gene selected from genes encoding HLA class II antigens HLA-DQA1 and HLA-DPA1, and a region of exon 2 to a 3' untranslated region in at least one of HLA-DRB1, HLA-DRB3, HLA-DRB4, HLA-DRB5, HLA-DQB1, and HLA-DPB1,
wherein amplifying comprises simultaneously amplifying by polymerase chain reaction (PCR) under identical reaction conditions in a single container the at least two genes in a test sample of the at least one of a transplant donor or a transplant recipient using the forward primers and reverse primers; and
wherein the PCR comprises a first set of at least 22 amplification cycles, each amplification cycle within the first set comprising a temperature of 98° C. for 10 seconds and 69° C. for 3 minutes, followed by a second set of at least eight amplification cycles, each amplification cycle of the second set comprising a temperature of 98° C. for 10 seconds and 60° C. for 3 minutes; and
(b) determining the nucleotide sequences of the amplified products.

7. The method of claim 6 further comprising the step of performing a homology search of the nucleotide sequences within a database.

8. The method of claim 6, wherein the forward primers consist of SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31 and the reverse primers consist SEQ ID NO: 2, SEQ ID NO: 6, SEQ ID NO: 7, SEQ ID NO: 10, SEQ ID NO: 11, SEQ ID NO: 15, SEQ ID NO: 16, SEQ ID NO: 17, SEQ ID NO 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

9. The method of claim 6, wherein the forward primers for the gene belonging to HLA class I consist of SEQ ID NO: 1, SEQ ID NO: 3, SEQ ID NO: 4, SEQ ID NO: 5, SEQ ID NO: 8, and SEQ ID NO: 9, wherein the reverse primers for the gene belonging to HLA class I consist of SEQ ID NO: 2, SEQ ID NO: 6, SEQ ID NO: 7, SEQ ID NO: 10, and SEQ ID NO: 11, and wherein the forward primers for the gene belonging to HLA class II consist of SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31, and the reverse primers for the gene belonging to HLA class II consist of SEQ ID NO: 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

10. The method of claim 6 wherein the set of forward primers has SEQ ID NO: 1, SEQ ID NO: 3, SEQ ID NO: 4, SEQ ID NO: 5, SEQ ID NO: 8, SEQ ID NO: 9, SEQ ID NO: 12, SEQ ID NO: 13, SEQ ID NO: 14, SEQ ID NO: 20, SEQ ID NO: 21, SEQ ID NO: 24, SEQ ID NO: 26, SEQ ID NO: 28, and SEQ ID NO: 31, and the set of reverse primers has SEQ ID NO: 2, SEQ ID NO: 6, SEQ ID NO: 7, SEQ ID NO: 10, SEQ ID NO: 11, SEQ ID NO 15, SEQ ID NO: 16, SEQ ID NO: 17, SEQ ID NO: 18, SEQ ID NO: 19, SEQ ID NO: 22, SEQ ID NO: 23, SEQ ID NO: 25, SEQ ID NO: 27, SEQ ID NO: 29, SEQ ID NO: 30, and SEQ ID NO: 32.

11. The method of claim 6 wherein the forward primers are selected from SEQ ID NO: 1, SEQ ID NO: 3, SEQ ID NO: 4, SEQ ID NO: 5, SEQ ID NO: 8, SEQ ID NO: 9, SEQ ID NO: 28, and SEQ ID NO: 31 and the reverse primers are selected from SEQ ID NO: 2, SEQ ID NO: 6, SEQ ID NO: 7, SEQ ID NO: 10, SEQ ID NO: 11, SEQ ID NO 29, SEQ ID NO: 30, and SEQ ID NO: 32.

* * * * *